US009155851B2

United States Patent
Briant et al.

(10) Patent No.: US 9,155,851 B2
(45) Date of Patent: Oct. 13, 2015

(54) BREATH ACTIVATED INHALER

(75) Inventors: John Briant, Hertfordshire (GB);
Patrick Campbell, Hertfordshire (GB);
Charles Cooke, Hertfordshire (GB);
Christopher Groombridge,
Hertfordshire (GB); Daniel James John,
Herfordshire (GB); **John Trevor
Penhallurick**, Hertfordshire (GB);
Nicholas Smartt, Hertfordshire (GB);
Nicholas Harrison, Cambridgeshire
(GB); William Bakewell, Hertfordshire
(GB)

(73) Assignee: ASTRAZENECA AB, Sodertalje (SE)

( * ) Notice: Subject to any disclaimer, the term of this patent is extended or adjusted under 35 U.S.C. 154(b) by 1101 days.

(21) Appl. No.: 13/123,714

(22) PCT Filed: Oct. 7, 2009

(86) PCT No.: PCT/SE2009/051111
§ 371 (c)(1),
(2), (4) Date: Nov. 15, 2011

(87) PCT Pub. No.: WO2010/042034
PCT Pub. Date: Apr. 15, 2010

(65) Prior Publication Data
US 2012/0048272 A1 Mar. 1, 2012

Related U.S. Application Data

(60) Provisional application No. 61/103,602, filed on Oct. 8, 2008.

(51) Int. Cl.
*A61M 15/00* (2006.01)

(52) U.S. Cl.
CPC ....... *A61M 15/0091* (2013.01); *A61M 15/0003* (2014.02); *A61M 15/0026* (2014.02);

(Continued)

(58) Field of Classification Search
CPC ....... A61M 15/0026; A61M 15/0091–15/0098
USPC ............. 128/200.14–200.23, 203.15, 128/203.18–203.24
See application file for complete search history.

(56) References Cited

U.S. PATENT DOCUMENTS

| 5,388,572 A | 2/1995 | Mulhauser et al. |
| 6,880,555 B1 * | 4/2005 | Brunnberg et al. ...... 128/203.12 |

(Continued)

FOREIGN PATENT DOCUMENTS

| DE | 10206045788 | 3/2008 |
| EP | 1522325 | 4/2005 |

(Continued)

OTHER PUBLICATIONS

International Search Report mailed on Jan. 22, 2010, in corresponding International Application PCT/SE2009/051111 (4 pages).

*Primary Examiner* — Valerie L Skorupa
(74) *Attorney, Agent, or Firm* — Finnegan, Henderson, Farabow, Garrett & Dunner LLP

(57) ABSTRACT

An inhaler including an outlet and a plurality of sealed compartments containing medicament is disclosed. An opening mechanism is provided to open the compartment presently aligned with the outlet. An indexing mechanism sequentially aligns the compartments with the outlet. A latch is provided for latching the opening mechanism in an energized position. The latch cannot latch the opening mechanism before the indexing mechanism has aligned the next compartment with the outlet. A method of priming an inhaler and a method of dispensing a medicament from an inhaler is also disclosed.

13 Claims, 8 Drawing Sheets

(52) U.S. Cl.
CPC ....... *A61M15/0043* (2014.02); *A61M 15/0045* (2013.01); *A61M 15/0048* (2014.02); *A61M 2202/064* (2013.01); *A61M 2205/073* (2013.01)

(56) References Cited

U.S. PATENT DOCUMENTS

| | | |
|---|---|---|
| 2005/0081851 A1 | 4/2005 | Young et al. |
| 2005/0172963 A1* | 8/2005 | Allan et al. .............. 128/203.15 |
| 2008/0001008 A1 | 1/2008 | Thoemmes et al. |
| 2008/0202515 A1 | 8/2008 | Hodson et al. |
| 2010/0083962 A1* | 4/2010 | Von Schuckmann .... 128/203.15 |
| 2010/0083964 A1* | 4/2010 | Brown et al. ............ 128/203.15 |
| 2010/0126507 A1* | 5/2010 | Lulla et al. ................ 128/203.15 |
| 2010/0163042 A1* | 7/2010 | Bhowmick et al. ...... 128/203.15 |

FOREIGN PATENT DOCUMENTS

| | | |
|---|---|---|
| WO | WO 02/24265 | 3/2002 |
| WO | WO 2006/000758 A1 | 1/2006 |
| WO | WO 2009/008001 | 1/2009 |
| WO | WO 2009/102275 | 8/2009 |

* cited by examiner

BREATH ACTIVATED INHALER

This is a U.S. National Phase Application of PCT/SE2009/051111, filed on Oct. 7, 2009, which claims the benefit of priority to U.S. Provisional Application No. 61/103,602, filed on Oct. 8, 2008, all of which are incorporated herein by reference.

TECHNICAL FIELD

The present invention relates to an inhaler comprising a plurality of sealed compartments containing medicament. The invention also relates to a method of priming an inhaler and a method of dispensing a medicament from an inhaler.

BACKGROUND OF THE INVENTION

There are different types of inhalers on the market. A pressurized Metered Dose Inhaler (pMDI) releases a fixed dose of substance in aerosol form. A powder inhaler generally releases a dose of powdered substance entrained in an air stream. In a powder inhaler the powder may be provided in a bulk container of the inhaler from which doses of powder are metered for dispensing. As an alternative to a bulk container, powder inhalers may comprise a single compartment or a plurality of compartments for containing one or more discrete doses of powdered substance. Such compartments may take the form of sealed blisters in a blister pack, a cavities-containing strip joined to a sealing strip or other suitable forms.

EP 1 220 698 discloses an inhaler for medicament in powder form. The medicament is arranged in the inhaler in a number of enclosures. When the airflow in the inhaler reaches a certain threshold value, a breath-activated activating means causes an elongated hollow body to pierce the enclosure so that the medicament is accessed. This is, for example, illustrated in FIGS. 3-6 of EP 1 220 698. After the medicament has been inhaled, the user closes a mouthpiece cover, which leads to retraction and latching of the hollow body into a firing position, and also movement of the enclosures one step. However, with that type of inhaler, if the mouthpiece cover is not properly closed, there may be a risk of the hollow body becoming retracted and latched although the inhaler has not been completely indexed to the next enclosure. Thus, the next time the user wants to inhale, the hollow body may risk either entering the same enclosure or just hit an intermediate portion between two enclosures, without delivering any medicament.

WO2009/008001A2 discloses a dry powder inhaler having a breath actuation feature. Opening a mouthpiece cap energises a spring. On inhalation, a flap is moved which triggers the release of the spring, driving a mechanism to (i) puncture a foil sealed medicament cavity and (ii) ratchet an indexer around a set of ratchet teeth on the periphery of a disc of medicament cavities. On closing the cap, the breath flap is re-set and the disc indexed around by one cavity. The disc is moved around progressively as the cap is closed and it is not clear at what point the breath flap is re-set, nor indeed how the breath flap is re-set. There is potential for the breath flap to be re-set before the disc has been fully indexed, e.g. if the cap is partly closed and then re-opened.

SUMMARY OF THE INVENTION

An object of the present invention is to avoid the drawback of the prior art inhalers. This and other objects, which will become apparent in the following, are accomplished by the inhaler and the methods defined in the accompanied claims.

The present invention is based on the insight that the risk of providing the inhaler in a ready to fire state although a medicament dose is not properly aligned can be reduced by providing a sequential resetting and latching of the opening mechanism, with appropriate timing in relation to the indexing mechanism.

According to a first aspect of the invention, an inhaler is provided. The inhaler comprises an outlet, a plurality of sealed compartments containing medicament, an opening mechanism (opening device) having an energized position in which it is biased towards an unloaded position, wherein during movement from the energized position to the unloaded position the opening mechanism opens a sealed compartment aligned with the outlet, an indexing mechanism (indexing device) for sequentially aligning the compartments with the outlet, wherein the indexing mechanism is adapted to align the next compartment with the outlet after the opening mechanism has been moved from the unloaded position to the energized position, and a latch having a first position, in which it latches the opening mechanism in the energized position, and a second position, in which it allows the opening mechanism to be in said unloaded position, wherein the latch is at least partly arranged in a flow path such that an inhalation flow through the flow path affects the latch to move from the first position to the second position, wherein the latch is prevented from returning to the first position before the indexing mechanism has aligned the next compartment with the outlet.

Thus, by delaying the latching of the opening mechanism in the energized position, the inhaler will not become primed in a ready to fire state before the next compartment is in place, i.e. aligned with the outlet. This means that the latch may suitably be adapted to move at the same time as or after the indexing mechanism has aligned the next compartment with the outlet. In this context the expression "aligned with the outlet" should be understood as having provided the compartment in a position for inhalation of the contained medicament through the outlet. The outlet may be a mouthpiece or a nasal adaptor.

The delayed latching of the opening mechanism may be accomplished in various ways. For instance, the inhaler may be provided with a number of user controls connected to the various mechanisms, in which case the controls may be arranged to only be operable in a determined order. In order to simplify for the user and reduce the number of user controls needed, the delay is suitably provided as a built-in function, which may be mechanical or electronic. According to at least one example embodiment of the invention, the inhaler comprises a catch having a preventing position, in which it prevents the latch to reach the first position, and a removed position, in which it allows the latch to reach the first position, wherein the catch is connected to and movable with the indexing mechanism. Since the indexing mechanism performs its aligning action after the opening mechanism has been moved to the energized position, the catch being connected to the indexing mechanism can be adapted to prevent the latching until the next compartment is in place.

Although a specifically designated user control may be provided for operating the inhaler, e.g. a separate lever or button at the inhaler housing, suitably, the movement of an outlet cover may be used for priming the inhaler. This is reflected in at least one example embodiment of the invention, according to which the inhaler comprises an outlet cover movable for alternatingly closing and opening the outlet, and a mechanical sequencing assembly connected to and movable with the outlet cover. Upon one of said closing or opening movements of the outlet cover, the connected mechanical sequencing assembly sequentially causes the opening mechanism to reach its energized position and then the indexing mechanism to align the next compartment with the outlet. For instance, after inhalation when a user closes the outlet cover so as to cover the outlet until the next time he/she will inhale, the closing motion will affect the mechanical sequencing assembly to cause the opening mechanism to reach its energized position and then the indexing mechanism to index the compartments one step. When the user later opens the outlet cover, the inhaler is already primed and the medicament becomes dispensed by an airflow caused by the inhalation effort of the user. An alternative would be to arrange for the mechanical sequencing assembly to perform its function when the user opens the outlet cover. The connection between the outlet cover and the mechanical sequencing assembly may suitably extend through one or more apertures in the inhaler housing.

The latch may also be affected by the mechanical sequencing assembly. Thus, the opening or closing movement of the outlet cover may be used to bias the latch towards its first position in which it latches the opening mechanism in its energized position. If the above-described preventing catch is present in the inhaler, it will counteract the bias. Once the catch is removed as the connected indexing mechanism is moved, the bias will cause the latch to move to the first position, thereby latching the opening mechanism.

The above-discussed mechanical sequencing assembly may be arranged to transmit a force to the opening mechanism and the indexing mechanism, respectively, at different points in time in order to obtain the delay. However, an alternative is to allow the forces to be transmitted substantially simultaneously while counteracting the force transmitted to the indexing mechanism in order to achieve the delay on the indexing mechanism. This is reflected in at least one example embodiment. In said embodiment, the mechanical sequencing assembly comprises a first force transmitting member adapted to move the opening mechanism from its unloaded position to its energized position. The mechanical sequencing assembly also comprises a second force transmitting member adapted to urge the indexing mechanism to advance the next compartment to be aligned with the outlet. There is also provided a counteracting member for temporarily counteracting the effect of the second force-transmitting member until the opening mechanism has reached its energized position.

The first force transmitting member may, for instance, comprise a pusher, such as a protrusion, ramp, curved wall or cam on a moving body, although various alternatives are conceivable. The movment of the first force transmitting member may suitably be a rotational movement although other directions, such as linear, are conceivable.

According to at least one example embodiment, the opening mechanism comprises a first spring, wherein said first force transmitting member pushes the opening mechanism against the force of the first spring to provide the opening mechanism in the energized position.

According to at least one example embodiment, the indexing mechanism comprises a drive member for advancing the compartments, and a second spring connected to the drive member, wherein the second force transmitting member is adapted to energize the second spring while the counteracting member temporarily prevents the compartments from moving.

According to at least one example embodiment, the mechanical sequencing assembly comprises a track. The counteracting member comprises a brake adapted to prevent the compartments from moving and a follower which is connected to the brake and which travels in a said track as the mechanical sequencing assembly moves in response to the movement of the outlet cover. When the follower reaches a point of release the connected brake is released, thereby enabling the compartments to move as a result of the force provided by the energized second spring via the drive member.

If the previously described catch is present in the inhaler, it may suitably be connected to the drive member, e.g. be formed in one piece with the drive member. Thus, if the drive member is motionless, so is the catch. Conversely, if the drive member moves, the catch moves. This is reflected in at least one example embodiment, according to which the catch is connected to the drive member, wherein when the counteracting member prevents the compartments from moving, the catch is maintained in its preventing position, and when the drive member is enabled to move the compartments, the catch is moved to its removed position. When the catch is in the removed position, the latch is allowed to reach its first position, in which it latches the opening mechanism in the energized position. In this way, the opening mechanism is not latched until the indexing is completed, thereby reducing the risk of empty (i.e. no dose) firing.

According to at least one example embodiment, the latch is biased towards its first position. The extent of the bias is suitably balanced against the expected airflow inducible by a user's inhalation. Thus, when an airflow exceeds a certain threshold the biasing force is overcome and the latch is moved to its second position. When the airflow drops under the threshold, the latch may return to its biased first position, however, there may be provided mechanisms, such as the previously described catch, for temporarily preventing such return motion in order to allow other parts (e.g. the opening mechanism and the compartments) of the inhaler to move before latching takes place. Eventually, the latch will be allowed to move to the first position for latching the opening mechanism in its energized position.

Although the latch may be designed as a one piece component, it may suitably comprise several components, such as one component being responsive to airflow, while another component engaging the opening mechanism. This is reflected in at least one example embodiment, according to which the latch comprises a first element and a second element, the first element being connected to the opening mechanism. The second element has a supporting position, in which it immobilizes the first element, thereby preventing the opening mechanism from moving to the unloaded position, and a non-supporting position, in which the first element is enabled to move, thereby allowing the biased opening mechanism to move to the unloaded position, wherein the second element is movable to the non-supporting position in response to the inhalation flow. In case the inhaler comprises the previously described catch, in its preventing position the catch would prevent the first element from becoming supported by the second element. Thus, the first element will only become supported by the second element when the catch is displaced to its removed position. Another conceivable alternative would be to affect the second element with the catch. For instance, when the catch is in its preventing position it could keep the second element in the non-supporting position, preventing it from reaching the supporting position. Thus, the first element cannot become supported and thus the opening mechanism cannot become latched. When the catch is then displaced to its removed position, the second element can return to the supporting position, wherein the first element can become supported, thereby latching the opening mechanism.

There are various conceivable motions for the first element. For instance, the first element may be slidably connected to the opening mechanism. Another alternative is rotatably connected, which is reflected in at least one example embodiment, wherein the first element comprises an elongated prop having a first end portion which is pivotable around an axis and a second end portion adapted to be supported by the second element. The pivot axis may be an axle forming part of or being connected to the opening mechanism.

Similarly, there are various conceivable motions for the second element. The second element may be slidably arranged within the inhaler housing, wherein a spring extending from the inhaler housing would urge the second element to slide to its supporting position. In another alternative, which is reflected in at least one example embodiment, the second element (e.g. designed as a rocker) is pivotable around an axis, wherein in response to the inhalation flow the second element is pivoted to allow the first element (e.g. a prop) to fall off its support.

The inventive idea is applicable in various inhaler configurations. For instance, it would be applicable in inhalers comprising compartments in the form of sealed blisters in a blister pack or in inhalers comprising a cavities-containing strip joined to a sealing strip or any other suitable configuration. According to at least one example embodiment, the inhaler comprises a base having said plurality of sealed compartments containing medicament, said compartments being in the form of cavities in the base, a plurality of foil portions comprising two sides, one side being attached to the base for sealing the medicament within the respective cavities, a plurality of separating elements, each separating element being attached to the other side of a respective foil portion for separating the foil portion from the cavity, wherein the opening mechanism comprises an actuator which is engagable with the separating element to cause the separating element to be moved away from the cavity.

Although the base may have a generally linear shape in some embodiments, e.g. for an inhaler having a relatively low number of doses, it may suitably have a generally circular rotatable disk configuration. The base may thus comprise a circumferentially-oriented sequence of cavities. Upon rotation of the disk the separating element next in turn is presented to the actuator. The rotatable disk may be connected to a separate manually operable lever. An alternative is to connect the rotation of the disk to the movement of the outlet cover. Thus, in either the course of opening or closing the outlet cover, the disk is rotated, thereby indexing the inhaler one step to the next dose. For instance, in an embodiment wherein the closing of the outlet cover causes the actuator to move to its energized position, the rotatable disk may also be moved (indexed) as a result of said closing.

In a multi-dose inhaler, the foil portions may be provided as one foil and, optionally, the foil portions may be defined by perforations or other material weakenings for facilitating removal of a foil portion from the cavity when the associated separating element is moved away from the base. As an alternative to a single foil, the foil portions may be applied in the form of individual patches. The foil portions may be attached to the base and the separating elements by welding, gluing or other suitable method. It should be noted that the terms "foil" and "foil portion" are not limited to a single material layer. On the contrary a foil or foil portion may comprise a plurality of layers. For instance, foil may comprise a metal layer which is coated with lacquer or polymer layer on one or both sides in any suitable combination in order to provide the desired stiffness, attachment capability, etc.

In order to separate a foil portion from the cavity it is sealing, the foil portion should be appropriately attached to its associated separating element. According to at least one example embodiment of the invention, the attachment force between the separating element and the respective associated foil portion is larger than the attachment force between the base and the foil portion, whereby movement of such a separating element away from its associated cavity causes the associated foil portion to become separated from the base.

Suitably, the contact area between a foil portion and its associated attached separating element is dimensioned in such way that no ruptured flow-obstructing foil parts will remain after the separation has occurred. In other words, the flow path downstream and upstream of the cavity opening should be free from any obstructing fringes of foil. Suitably, on the base, the flow path upstream and downstream of the cavity opening is completely foil free after the separation has occurred. This may be accomplished by designing the separating element with longer (or equal) extension in the flow path direction than that of the foil portion. Since the foil portion extends across the cavity opening in order to seal the cavity, the attached separating element should also extend at least across the cavity opening. As mentioned previously, the foil portions may form part of one covering foil provided with perforations or weakenings which define the foil portions. Such perforations would be present between the cavity openings, and when the foil portions are ruptured at those perforations or weakenings any fringes would be located laterally of the cavity viewed from a flow direction perspective, and consequently no obstructing fringes would be present upstream or downstream of the cavity.

There are various ways to obtain a larger attachment force at the separating element/foil portion interface than at the foil portion/base interface. According to at least one example embodiment of the invention, the contact surface between a separating element and its associated foil portion is larger than the contact surface between that foil portion and the base. In other words the separating element/foil portion interface is larger than the foil portion/base interface. If the separating element covers the entire foil portion, then the contact surface will automatically be larger between the separating element and the foil portion than the contact surface between the foil portion and the base, because the piece of the foil portion located directly above the cavity opening is not attached to anything and only the surrounding area of the foil is attached to the base.

Another way to obtain different attachment forces is considered in at least one other example embodiment of the invention. The foil portions may comprise a first coating layer to which the base is attached and a second coating layer to which the separating elements are attached, wherein the tensile strength of the second coating layer is larger than the tensile strength of the first coating layer. The layers can provide different bonding properties, e.g. welds of different types of material, or glues of different types or amounts, or any combination thereof.

Other ways to obtain the difference in attachment forces could be to provide the separating element with specially designed geometric features, e.g. grooves into which the foil may be attached or other features that e.g. pierce the foil to create a firm grip.

Although the foil portion may be folded into grooves of the separating element or otherwise curved around the separating element e.g. to increase the attachment area, the foil portion may suitably just be flat, i.e. only extending in a single plane parallel to the base. This enables a simple assembling of the separating elements to the foil portions. When they have become assembled the foil may be attached to the base. An alternative would be to first attach the foil portions to the base, and then attach the separating elements onto the respective foil portions.

Suitably, the stiffness of the separating elements is substantially larger than the stiffness of the foil portions, wherein the separating elements enable the foil portions to perform a rigid body motion, and may thus become lifted or snapped off the base rather than peeled off.

Although the above exemplified embodiments have discussed one cavity having one associated separating element, an alternative would be to have two cavities having one common associated separating element. For instance, if two incompatible drug components are to be inhaled essentially simultaneously, they may suitably be provided in two separate cavities. The two cavities may be covered and sealed by one common foil portion (or one foil portion each), which in turn is attached to a common associated separating element extending across both cavities. Thus, when the separating element is moved away from the cavity, it will bring along the foil portion, uncovering both cavities from which the drug components can be entrained in an inhalation flow. The cavities could either be located in series in the base, i.e. one cavity being downstream of the other one, or they could be located in parallel, i.e. the inhalation flow reaches the cavities essentially simultaneously.

Although a sealing foil portion may be beneficial for reducing the risk of moisture ingress, according to at least example embodiment, removable covering elements (rather than separating elements) may be attached (e.g. glued or welded) directly to the base to cover the respective cavities, without the presence of said foil portions.

The inhaler may contain various drugs and/or bioactive agents to be inhaled.

The bioactive agent may be selected from any therapeutic or diagnostic agent. For example it may be from the group of antiallergics, bronchodilators, bronchoconstrictors, pulmonary lung surfactants, analgesics, antibiotics, leukotrine inhibitors or antagonists, anticholinergics, mast cell inhibitors, antihistamines, antiinflammatories, antineoplastics, anaesthetics, anti-tuberculars, imaging agents, cardiovascular agents, enzymes, steroids, genetic material, viral vectors, antisense agents, proteins, peptides and combinations thereof.

Examples of specific drugs which can be incorporated in the inhalation device according to the invention include mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, Symbicort™ (budesonide and formoterol), terbutaline, terbutaline sulphate, salbutamol base and sulphate, fenoterol, 3-[2-(4-Hydroxy-2-oxo-3H-1,3-benzothiazol-7-yl)ethylamino]-N-[2-[2-(4-methylphenyl)ethoxy]ethyl]propanesulphonamide, hydrochloride. All of the above compounds can be in free base form or as pharmaceutically acceptable salts as known in the art.

Combinations of drugs may also be employed, for example formoterol/budesonide; formoterol/fluticasone; formoterol/mometasone; salmeterol/fluticasone; formoterol/tiotropium salts; zafirlukast/formoterol, zafirlukast/budesonide; montelukast/formoterol; montelukast/budesonide; loratadine/montelukast and loratadine/zafirlukast.

Further combinations include tiotropium and fluticasone, tiotropium and budesonide, tiotropium and mometasone, mometasone and salmeterol, formoterol and rofleponide, salmeterol and budesonide, salmeterol and rofleponide, and tiotropium and rofleponide.

According to a second aspect of the invention, there is provided a method of priming an inhaler which comprises an outlet, a sequence of sealed compartments containing medicament and an opening mechanism for opening that sealed compartment which is aligned with the outlet, the method comprising:

moving the opening mechanism to an energized position in which it is biased towards an unloaded position, aligning the next compartment with the outlet after said moving of the opening mechanism, latching the opening mechanism in its energized position after said aligning of the next compartment.

This operating sequence reduces the risk of firing without dose delivery. The term "next compartment" means the compartment which is in turn to be aligned with the outlet. For instance, assuming that a set of compartments Nos. 1, 2, 3, 4, 5 are to be aligned in that order sequentially with the outlet and that presently compartment No. 3 is aligned with the outlet, the "next compartment" will be compartment No. 4.

According to a third aspect of the invention, there is provided a method of dispensing a medicament from an inhaler, comprising the method of priming of the second aspect and further comprising:

providing an airflow through the inhaler to activate the unlatching of the opening mechanism, unlatching the opening mechanism in response to said airflow, thereby allowing the opening mechanism to move to its unloaded position, opening, during the movement of the opening mechanism to its unloaded position, the sealed compartment aligned with the outlet, and dispensing the medicament entrained by the airflow.

It should be understood that the methods of the second and third aspect of the invention, encompass and may be implemented with any embodiments or any features described in connection with the inhaler of the first aspect of the invention, as long as those embodiments or features are compatible with the methods of the second and third aspect.

The medicament may comprise various active ingredients (possibly together with other ingredients, such as e.g. carrier particles of lactose). The active ingredient may be selected from any therapeutic or diagnostic agent. For example, the active ingredient may be an antiallergic, a bronchodilator (e.g. a beta2-adrenoceptor agonist or a muscarinic antagonist), a bronchoconstrictor, a pulmonary lung surfactant, an analgesic, an antibiotic, a mast cell inhibitor, an antihistamine, an anti-inflammatory, an antineoplastic, an anaesthetic, an anti-tubercular, an imaging agent, a cardiovascular agent, an enzyme, a steroid, genetic material, a viral vector, an antisense agent, a protein, a peptide, a non-steroidal glucocorticoid Receptor (GR Receptor) agonist, an antioxidant, a chemokine antagonist (e.g. a CCR1 antagonist), a corticosteroid, a CRTh2 antagonist, a DP1 antagonist, an Histone Deacetylase Inducer, an IKK2 inhibitor, a COX inhibitor, a lipoxygenase inhibitor, a leukotriene receptor antagonist, an MPO inhibitor, a p38 inhibitor, a PDE inhibitor, a PPARγ agonist, a protease inhibitor, a statin, a thromboxane antagonist, a vasodilator, an ENAC blocker (Epithelial Sodium-channel blocker) and combinations thereof.

Examples of specific active ingredients that can be incorporated in the inhaler include:

(i) antioxidants:—Allopurinol, Erdosteine, Mannitol, N-acetyl cysteine choline ester, N-acetyl cysteine ethyl ester, N-Acetylcysteine, N-Acetylcysteine amide and Niacin;

(ii) chemokine antagonists:—BX471 ((2R)-1-[[2-[(aminocarbonyl)amino]-4-chlorophenoxy]acetyl]-4-[(4-fluorophenyl)methyl]-2-methylpiperazine monohydrochloride), CCX634, N-{2-[((2S)-3-{[1-(4-chlorobenzyl) piperidin-4-yl]amino}-2-hydroxy-2-methylpropyl)oxy]-4-hydroxyphenyl}acetamide (see WO 2003/051839), and 2-{2-Chloro-5-{[(2S)-3-(5-chloro-1'H,3H-spiro[1-benzofuran-2,4'-piperidin]-1'-yl)-2-hydroxypropyl]oxy}-4-[(methylamino)carbonyl]phenoxy}-2-methylpropanoic acid (see WO 2008/010765), 656933 (N-(2-bromophenyl)-N'-(4-cyano-1H-1,2,3-benzotriazol-7-yl)urea), 766994 (4-({[({[(2R)-4-(3,4-dichlorobenzyl)morpholin-2-yl]methyl}amino)carbonyl]-amino}methyl)benzamide), CCX-282, CCX-915, Cyanovirin N, E-921, INCB-003284, INCB-9471, Maraviroc, MLN-3701, MLN-3897, T-487 (N-{1-[3-(4-ethoxyphenyl)-4-oxo-3,4-dihydropyrido[2,3-d]pyrimidin-2-yl]ethyl}-N-(pyridin-3-ylmethyl)-2-[4-(trifluoromethoxy)phenyl]acetamide) and Vicriviroc (iii) Corticosteroids:—Alclometasone dipropionate, Amelometasone, Beclomethasone dipropionate, Budesonide, Butixocort propionate, Ciclesonide, Clobetasol propionate, Desisobutyrylciclesonide, Etiprednol dicloacetate, Fluocinolone acetonide, Fluticasone Furoate, Fluticasone propionate, Loteprednol etabonate (topical) and Mometasone furoate.

(iv) DP1 antagonisits:—L888839 and MK0525;

(v) Histone deacetylase inducers:—ADC4022, Aminophylline, a Methylxanthine or Theophylline;

(vi) IKK2 inhibitors:—2-{[2-(2-Methylamino-pyrimidin-4-yl)-1H-indole-5-carbonyl]-amino}-3-(phenyl-pyridin-2-yl-amino)-propionic acid;

(vii) COX inhibitors:—Celecoxib, Diclofenac sodium, Etodolac, Ibuprofen, Indomethacin, Meloxicam, Nimesulide, OC1768, OC2125, OC2184, OC499, OCD9101, Parecoxib sodium, Piceatannol, Piroxicam, Rofecoxib and Valdecoxib;

(viii) Lipoxygenase inhibitors:—Ajulemic acid, Darbufelone, Darbufelone mesilate, Dexibuprofen lysine (monohydrate), Etalocib sodium, Licofelone, Linazolast, Lonapalene, Masoprocol, MN-001, Tepoxalin, UCB-35440, Veliflapon, ZD-2138, ZD-4007 and Zileuton ((±)-1-(1-Benzo[b]thien-2-ylethyl)-1-hydroxyurea);

(ix) Leukotriene receptor antagonists:—Ablukast, Iralukast (CGP 45715A), Montelukast, Montelukast sodium, Ontazolast, Pranlukast, Pranlukast hydrate (mono Na salt), Verlukast (MK-679) and Zafirlukast;

(x) MPO Inhibitors:—Hydroxamic acid derivative (N-(4-chloro-2-methyl-phenyl)-4-phenyl-4-[[(4-propan-2-ylphenyl)sulfonylamino]methyl]piperidine-1-carboxamide), Piceatannol and Resveratrol;

(xi) Beta2-adrenoceptor agonists:—metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol, indacaterol, salmeterol (e.g. as xinafoate), bambuterol (e.g. as hydrochloride), carmoterol, indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino)hexyl]oxy}-butyl)-benzenesulfonamide; 3-(4-{[6-({(2R)-2-hydroxy-2-[4-hydroxy-3-(hydroxy-methyl)phenyl]ethyl}amino)-hexyl]oxy}butyl)benzenesulfonamide; GSK 159797, GSK 159802, GSK 597901, GSK 642444, GSK 678007; and a compound selected from N-[2-(Diethylamino) ethyl]-N-(2-{[2-(4-hydroxy-2-oxo-2,3-dihydro-1,3-benzothiazol-7-yl)ethyl]amino}ethyl)-3-[2-(1-naphthyl) ethoxy]propanamide, N-[2-(Diethylamino)ethyl]-N-(2-{[2-(4-hydroxy-2-oxo-2,3-dihydro-1,3-benzothiazol-7-yl)ethyl]amino}ethyl)-3-[2-(3-chlorophenyl)ethoxy]propanamide, 7-[(1R)-2-({2-[(3-{[2-(2-Chlorophenyl)ethyl] amino}propyl)thio]ethyl}amino)-1-hydroxyethyl]-4-hydroxy-1,3-benzothiazol-2(3H)-one, and N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl] amino}ethyl)-β-alaninamide or a pharmaceutically acceptable salt thereof (e.g. wherein the counter ion is hydrochloride (for example a monohydrochloride or a dihydrochloride), hydrobromide (for example a monohydrobromide or a dihydrobromide), fumarate, methanesulphonate, ethanesulphonate, benzenesulphonate, 2,5-dichlorobenzenesulphonate, p-toluenesulphonate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), D-mandelate, L-mandelate, cinnamate or benzoate.)

(xii) Muscarinic antagonists:—Aclidinium bromide, Glycopyrrolate (such as R,R-, R,S-, S,R-, or S,S-glycopyrronium bromide), Oxitropium bromide, Pirenzepine, telenzepine, Tiotropium bromide, 3(R)-1-phenethyl-3-(9H-xanthene-9-carbonyloxy)-1-azoniabicyclo[2.2.2]octane bromide, (3R)-3-[(2S)-2-cyclopentyl-2-hydroxy-2-thien-2-ylacetoxy]-1-(2-phenoxyethyl)-1-azoniabicyclo[2.2.2]actane bromide, a quaternary salt (such as [2-((R)-Cyclohexyl-hydroxy-phenyl-methyl)-oxazol-5-ylmethyl]-dimethyl-(3-phenoxy-propyl)-ammonium salt, [2-(4-Chloro-benzyloxy)-ethyl]-[2-(R)-cyclohexyl-hydroxy-phenyl-methyl)-oxazol-5-ylmethyl]-dimethyl-ammonium salt and (R)-1-[2-(4-Fluoro-phenyl)-ethyl]-3-((S)-2-phenyl-2-piperidin-1-yl-propionyloxy)-1-azonia-bicyclo[2.2.2]octane salt wherein the counter-ion is, for example, chloride, bromide, sulfate, methanesulfonate, benzenesulfonate (besylate), toluenesulfonate (tosylate), napthalenebissulfonate (napadisylate or hemi-napadisylate), phosphate, acetate, citrate, lactate, tartrate, mesylate, maleate, fumarate or succinate)

(xiii) p38 Inhibitors:—681323, 856553, AMG548 (2-[[(2S)-2-amino-3-phenylpropyl]amino]-3-methyl-5-(2-naphthalenyl)-6-(4-pyridinyl)-4(3H)-pyrimidinone), Array-797, AZD6703, Doramapimod, KC-706, PH 797804, R1503, SC-80036, SCIO469, 6-chloro-5-[[(2S,5R)-4-[(4-fluorophenyl)methyl]-2,5-domethyl-1-piperazinyl]carbonyl]-N,N,1-trimethyl-α-oxo-1H-indole-3-acetamide, VX702 and VX745 (5-(2,6-dichlorophenyl)-2-(phenylthio)-6H-pyrimido[1,6-b]pyridazin-6-one);

(xiv) PDE Inhibitors:—256066, Arofylline (3-(4-chlorophenyl)-3,7-dihydro-1-propyl-1H-Purine-2,6-dione), AWD 12-281 (N-(3,5-dichloro-4-pyridinyl)-1-[(4-fluorophenyl) methyl]-5-hydroxy-α-oxo-1H-indole-3-acetamide), BAY19-8004 (Bayer), CDC-801 (Calgene), Celgene compound ((βR)-β-(3,4-dimethoxyphenyl)-1,3-dihydro-1-oxo-2H-isoindole-2-propanamide), Cilomilast (cis-4-cyano-4-[3-(cyclopentyloxy)-4-methoxyphenyl]-cyclohexanecarboxylic acid), 2-(3,5-dichloro-4-pyridinyl)-1-(7-methoxyspiro[1,3-benzodioxole-2,1'-cyclopentan]-4-yl)ethanone (CAS number 185406-34-2)), (2-(3,4-difluorophenoxy)-5-fluoro-N-[cis-4-[(2-hydroxy-5-methylbenzoyl)amino]cyclohexyl]-)-3-pyridinecarboxamide), (2-(3,4-difluorophenoxy)-5-fluoro-N-[cis-4-[[2-hydroxy-5-(hydroxymethyl)benzoyl]amino] cyclohexyl]-3-pyridinecarboxamide,), CT2820, GPD-1116, Ibudilast, IC 485, KF 31334, KW-4490, Lirimilast ([2-(2,4-dichlorobenzoyl)-6-[(methylsulfonyl)oxy]-3-benzofuranyl]-urea), (N-cyclopropyl-1,4-dihydro-4-oxo-1-[3-(3-pyridinylethynyl)phenyl]-)-1,8-naphthyridine-3-carboxamide), (N-(3,5-dichloro-4-pyridinyl)-4-(difluoromethoxy)-8-[methylsulfonyl)amino])-1-dibenzofurancarboxamide), ONO6126, ORG 20241 (4-(3,4-dimethoxyphenyl)-N-hydroxy-)-2-thiazolecarboximidamide), PD189659/PD168787 (Parke-Davis), Pentoxifylline (3,7-dihydro-3,7-dimethyl-1-(5-oxohexyl)-)-1H-purine-2,6-dione), compound (5-fluoro-N-[4-[(2-hydroxy-4-methyl-benzoyl)amino]cyclohexyl]-2-(thian-4-yloxy)pyridine-3-carboxamide), Piclamilast (3-(cyclopentyloxy)-N-(3,5-dichloro-4-pyridinyl)-4-methoxy-benzamide), PLX-369 (WO 2006026754), Roflumilast (3-(cyclopropylmethoxy)-N-(3,5-dichloro-4-pyridinyl)-4-(difluoromethoxy)benzamide), SCH 351591 (N-(3,5-dichloro-1-oxido-4-pyridinyl)-8-methoxy-2-(trifluoromethyl)-5-quinolinecarboxamide), SelCID™ CC-10004 (Calgene), T-440 (Tanabe), Tetomilast (6-[2-(3,4-diethoxyphenyl)-4-thiazolyl]-2-pyridinecarboxylic acid), Tofimilast (9-cyclopentyl-7-ethyl-6,9-dihydro-3-(2-thienyl)-5H-pyrazolo[3,4-c]-1,2,4-triazolo[4,3-a]pyridine), TPI 1100, UCB 101333-3 (N,2-dicyclopropyl-6-(hexahydro-1H-azepin-1-yl)-5-methyl-4-pyrimidinamine), V-11294A (Napp), VM554/VM565 (Vernalis), and Zardaverine (6-[4-(difluoromethoxy)-3-methoxyphenyl]-3(2H)-pyridazinone).

(xv) PDE5 Inhibitors:—Gamma-glutamyl[s-(2-iodobenzyl)cysteinyl]glycine, Tadalafil, Vardenafil, sildenafil, 4-phenyl-methylamino-6-chloro-2-(1-imidazolyl)-quinazoline, 4-phenyl-methylamino-6-chloro-2-(3-pyridyl)-quinazoline, 1,3-dimethyl-6-(2-propoxy-5-methanesulphonylamidophenyl)-1,5-dihydropyrazolo[3,4-d]pyrimidin-4-one and 1-cyclopentyl-3-ethyl-6-(3-ethoxy-4-pyridyl)-pyrazolo[3,4-d]pyrimidin-4-one;

(xvi) PPARγ agonists:—Pioglitazone, Pioglitazone hydrochloride, Rosiglitazone Maleate, Rosiglitazone Maleate ((−)-enantiomer, free base), Rosiglitazone maleate/Metformin hydrochloride and Tesaglitizar;

(xvii) Protease Inhibitors:—Alpha1-antitrypsin proteinase Inhibitor, EPI-HNE4, UT-77, ZD-0892, DPC-333, Sch-709156 and Doxycycline;

(xviii) Statins:—Atorvastatin, Lovastatin, Pravastatin, Rosuvastatin and Simvastatin (xix) Thromboxane Antagonists: Ramatroban and Seratrodast;

(xx) Vasodilators:—A-306552, Ambrisentan, Avosentan, BMS-248360, BMS-346567, BMS-465149, BMS-509701, Bosentan, BSF-302146 (Ambrisentan), Calcitonin Gene-related Peptide, Daglutril, Darusentan, Fandosentan potassium, Fasudil, Iloprost, KC-12615 (Daglutril), KC-12792 2AB (Daglutril), Liposomal treprostinil, PS-433540, Sitaxsentan sodium, Sodium Ferulate, TBC-11241 (Sitaxsentan), TBC-3214 (N-(2-acetyl-4,6-dimethylphenyl)-3-[[(4-chloro-3-methyl-5-isoxazolyl)amino]sulfonyl]-2-thiophenecarboxamide), TBC-3711, Trapidil, Treprostinil diethanolamine and Treprostinil sodium;

(xxi) ENACs:—Amiloride, Benzamil, Triamterene, 552-02, PSA14984, PSA25569, PSA23682 and AER002.

The inhaler may contain a combination of two or more active ingredients, for example a combination of two or more of the specific active ingredients listed in (i) to (xxi) herein above.

In one embodiment the inhaler contains an active ingredient selected from mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, terbutaline, terbutaline sulphate, salbutamol base and sulphate, fenoterol, 3-[2-(4-Hydroxy-2-oxo-3H-1,3-benzothiazol-7-yl)ethylamino]-N-[2-[2-(4-methylphenyl)ethoxy]ethyl]propane-sulphonamide, hydrochloride, indacaterol, aclidinium bromide, N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide); N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate); a [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate); a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate); or a combination of any two or more thereof.

Specific combinations of active ingredients which may be incorporated in the inhaler include:—

(a) formoterol (e.g. as fumarate) and budesonide;
(b) formoterol (e.g. as fumarate) and fluticasone;
(c) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide) and a [2-(4-Chloro-benzyloxy)-ethyl]-[2-((R)-cyclohexyl-hydroxy-phenyl-methyl)-oxazol-5-yl-methyl]-dimethyl-ammonium salt (e.g. hemi-naphthalene-1,5-disulfonate);
(d) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide) and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate);
(e) N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate) and [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate);

N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate) and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate).

DETAILED DESCRIPTION OF THE DRAWINGS

Figure 1:
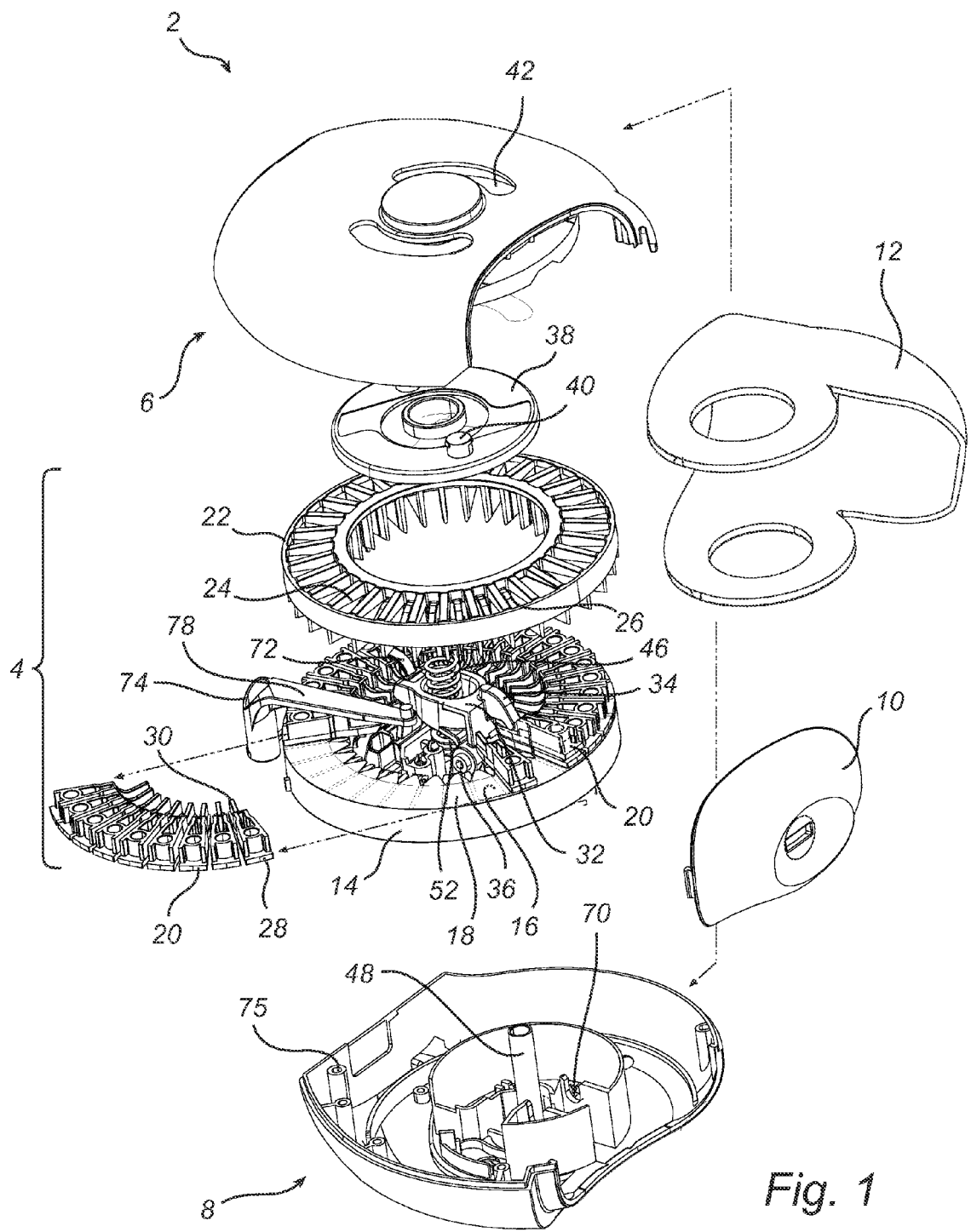
FIG. 1 is an exploded view of an inhaler according to at least one example embodiment of the invention.

FIG. 1 is an exploded view of an inhaler 2 according to at least one example embodiment of the invention. The inhaler 2 comprises a dose dispensing assembly 4 having a general disk configuration, an upper housing portion 6, a lower housing portion 8, an outlet herein represented in the form of a mouthpiece 10, and an outlet cover 12.

The dose dispensing assembly 4 comprises a circular base 14 which has a plurality of sequentially arranged cavities 16 along the circular extension of the base. The cavities 16 can be provided with medicament, such as in dry powder form, and are sealed by foil portions 18, thus providing sealed compartments. The foil portions 18 are either part of one common foil or provided as separate patches. In the shown example, perforations have been provided to define the foil portions 18 and to facilitate separation from the base 14. Above each cavity 16, a respective associated separating element 20 is attached to the upper side of the foil portion 18. The separating elements 20 are attached by any suitable type of bonding, welding, gluing, etc. to the respective foil portions 18. Upwards movement or lifting of a separating element 20 causes the attached foil portion 18 to become separated from the cavity 16.

A circular guide structure 22 is provided above the separating elements 20. The guide structure 22 comprises a plurality of guide sections 24 divided by vertically extending walls, each guide section 24 being associated with a respective separating element 20. When a separating element 20 is lifted from the cavities-holding base 14, the associated guide section 24 will guide the upwards movement of the separating element 20. Each guide section 24 is provided with a counteracting element, such as a blade spring 26. After a separating element 20 has been lifted and medicament in the opened cavity 16 has been entrained in the inhalation airflow and the separating element 20 has returned to the base 14, the blade spring 26 will keep the lifted separating element 20 in contact with the base 14 to cover the cavity 16. This will make it difficult for any remaining powder to exit the covered used cavity 16, thus reducing the risk of dose variation which could occur if such remaining powder would be entrained in a following inhalation. It also reduces the risk of remaining powder exiting the cavity 16 and jamming mechanical components in the inhaler or the risk of the separating element creating a rattling noise which would be undesirable for the user. The vertical walls dividing the circular guide structure 22 into guide sections 24 function as lateral flow path defining elements. Thus, an inhalation airflow is prevented from deviating sideways once it reaches the cavity area of the base 14 and will be led to the mouthpiece 10. An alternative would be to have shorter vertical walls, in which case neighbouring separating elements 20 could have the function of lateral flow path defining elements.

Each separating element 20 has a base-covering portion 28 which is in register with a respective cavity 16 in the base. Additionally, each separating element 20 has a centrally projecting portion 30. An opening mechanism comprising an actuator 32 for lifting the separating elements 20 is provided. The actuator is herein represented in the form of a pivotable lever provided with jaws 34 for gripping the centrally projecting portions 30 of the separating elements 20. The actuator 32 has an energized position (FIGS. 2 and 6) in which the jaws 34 are in a lowered position and, after pivoting about a pivot axel 36, an unloaded position (FIGS. 3 and 7) in which the jaws 34 are in a raised position. The actuator 32 with its jaws 34 is only pivotable around the horizontal axel 36 and will thus remain facing the mouthpiece 12 during operation of the inhaler 2.

Returning to FIG. 1, a generally disk-shaped insert 38 is provided under the upper housing portion 6. The upper side of the insert 38 is provided with two pegs 40. The pegs 40 extend upwardly through respective arcuate openings 42 in the upper housing portion 6 and are connected to the outlet cover 12. As the outlet cover 12 is rotated, the pegs 40 will through the arcuate openings 42 transmit the motion to the insert 38 which will also rotate. The underside of the insert 38 is provided with a first force transmitting member, herein illustrated in the form of a cam 44 (see FIG. 4), which will convert the rotating motion to a linear force affecting the jaws 34 of the actuator 32 in order to return the actuator 32 from its unloaded position to its energized position. As the cam 44 comes into contact with the jaws 34 of the actuator 32 (see FIG. 5), the actuator 32 will be moved radially towards the separating element 20 and will rotate around its pivot axel 36. Also, the jaws 34 will drop down to the primed or energized position of the actuator 32 (see FIG. 2). The lowering of the jaws 34 will be against the force of a coil spring 46 which is biased to raise the jaws 34 to the unloaded position. The coil spring 46 is wound around a post 48 projecting upwardly from the lower housing portion 8.

Figure 4:
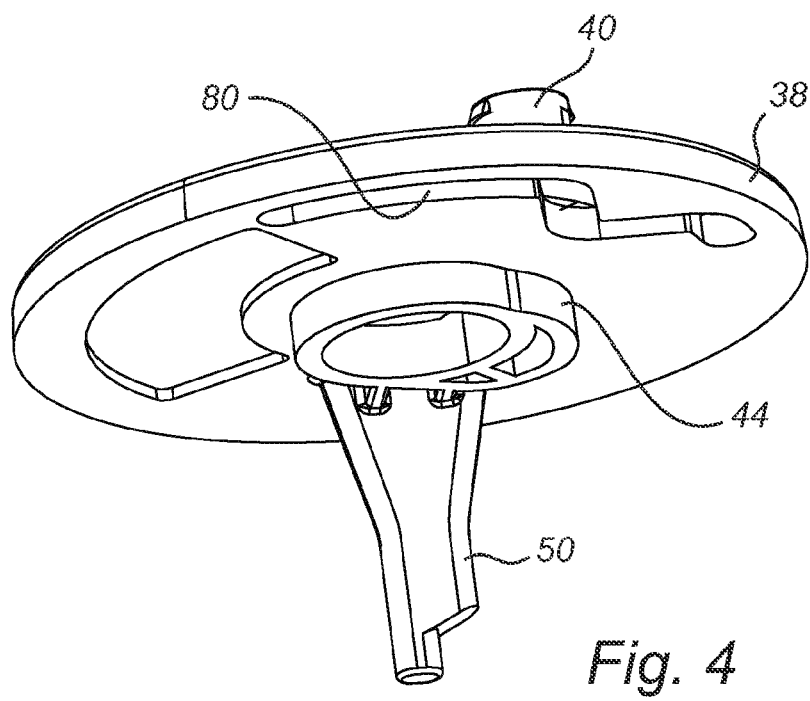
FIGS. 4 to 8 and 11 illustrate various details of the inhaler.
Figure 6:
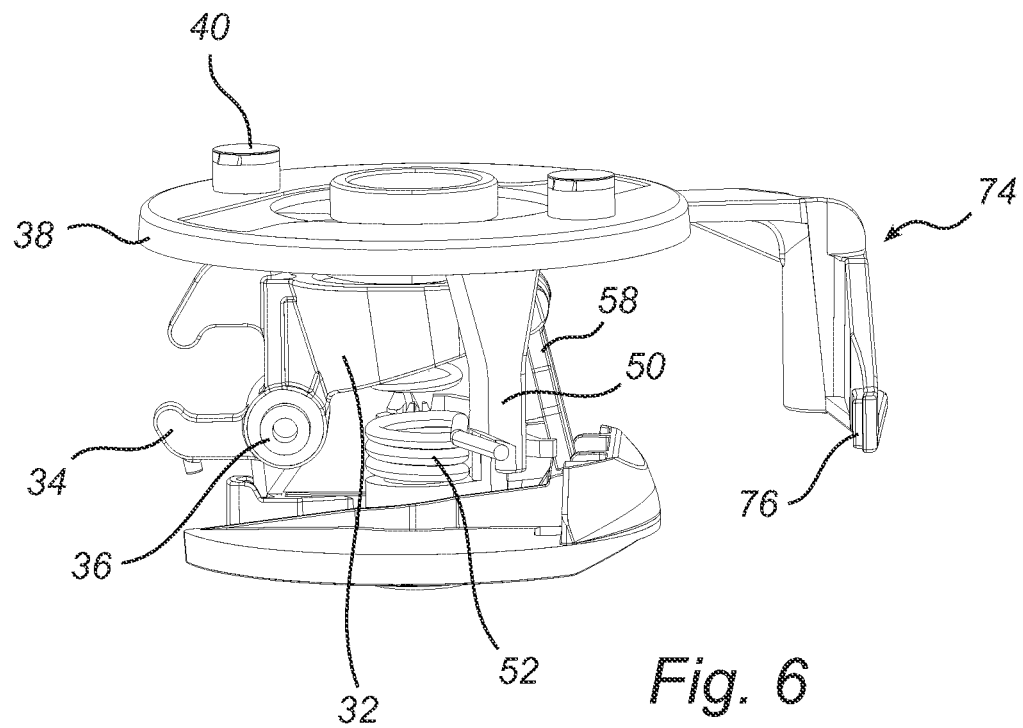
Figure 7:
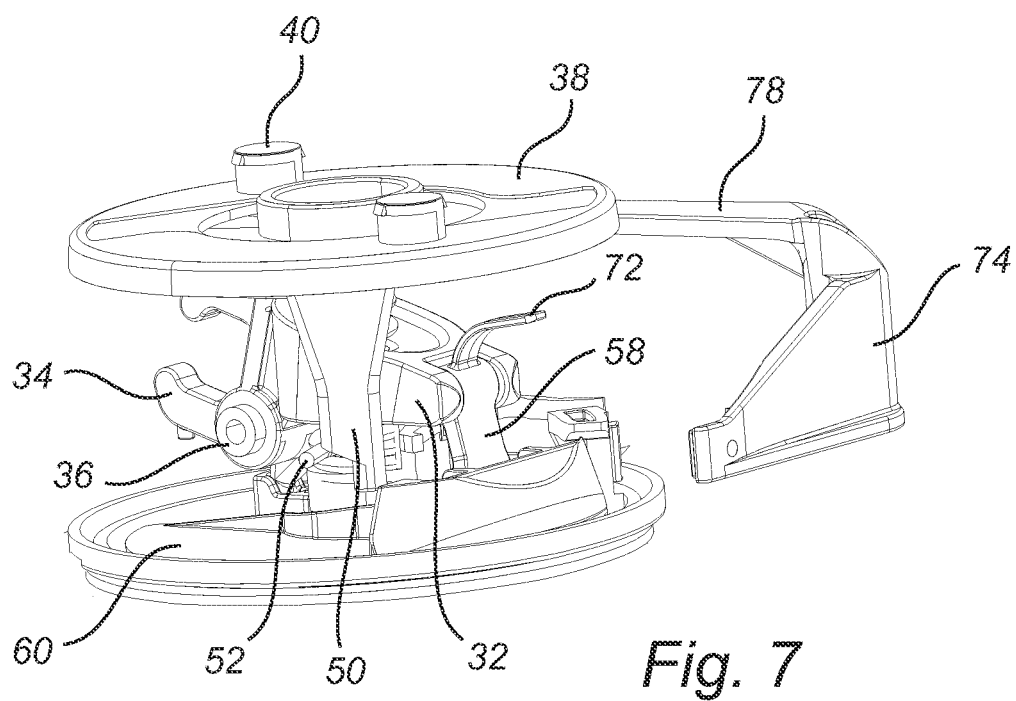
Figure 8:
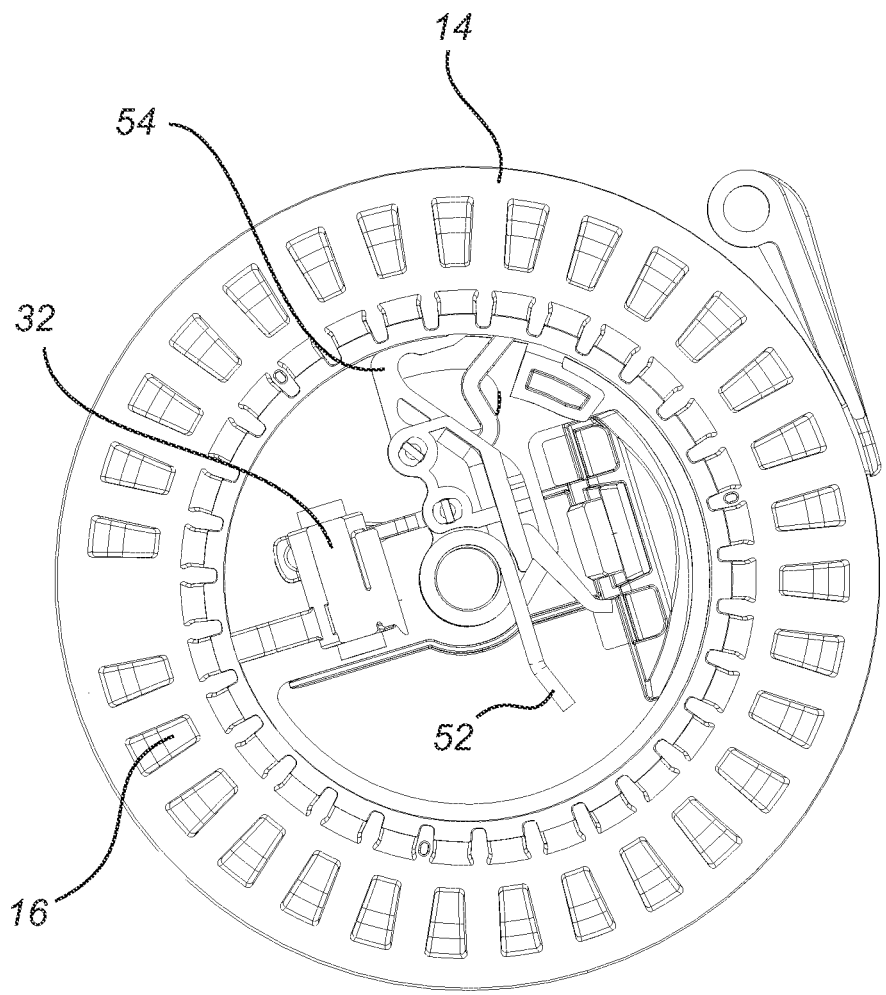

As illustrated in FIGS. 4, 6 and 7, the underside of the insert 38 is also provided with a projecting second force transmitting member 50 which is configured and adapted to engage an end of a torsion spring 52 located under the coil spring 46 and around the same post 48. The torsion spring 52 is connected to a drive member 54 for rotatingly advancing the cavities 16 by one increment at a time, so as to each time bring an unopened cavity in alignment with the mouthpiece 10. The drive member is best seen in FIGS. 8, 9, 10 and 11.

Figure 2:
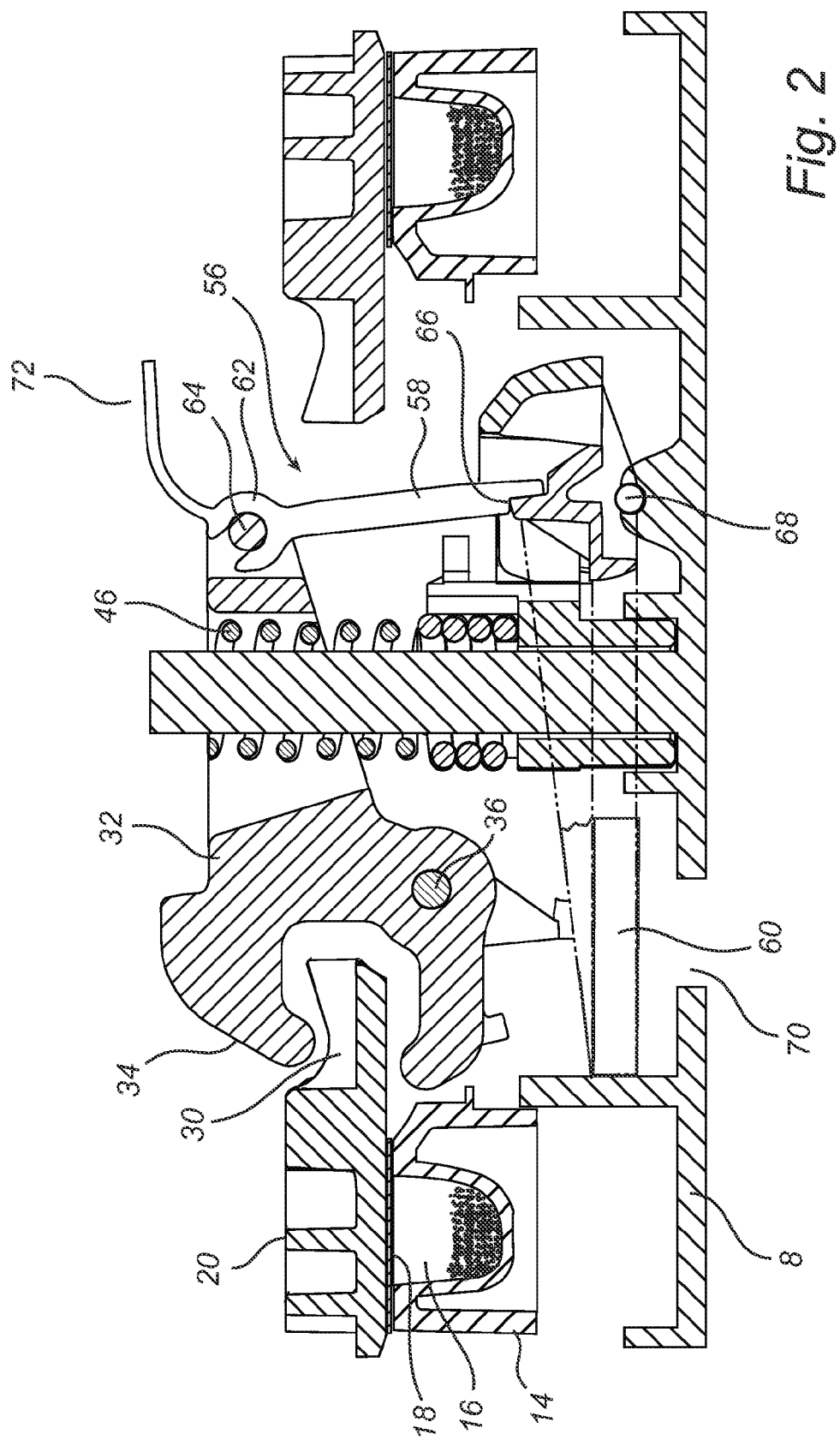
FIG. 2 is a cross-sectional view of selected details of the inhaler.

A latch 56 is provided to keep the actuator in the energized position, which is clearer from FIG. 2. The latch 56 comprises a first element in the form of an elongated prop 58 and a second element in the form of a flap 60. The elongated prop 58 has a first end portion 62 which is pivotable around a first horizontal axle 64 near that end of the actuator 32 which is located distally to the mouthpiece 10 (the jaws 34 being located proximally to the mouthpiece 10). The elongated prop 58 has a second end portion 66 adapted to be supported by the flap 60. The flap 60 is pivotable around a second horizontal axle 68. The flap covers a number of air inlets 70 (FIGS. 1-3) provided in the lower housing portion 8. Air is allowed to enter the inhaler 2 through said air inlets 70 when the user inhales through the mouthpiece 10 (outlet).

FIG. 2 is a cross-sectional view of selected details of the inhaler, wherein the inhaler is in a primed state, i.e. the actuator 32 is latched in an energized position. Thus, the jaws 34 of the actuator 32 have been lowered against the force of the coil spring 46 and now enclose the centrally projecting portion 30 of a separating element 20 aligned with the mouthpiece. The second end portion 66 of the elongated prop 58 is supported by a mating portion of the flap 60. The latch 56 comprising the prop 58 and the flap 60 is now in its first position, in which it latches the actuator 32 in the energized position. The latch 56 is biased towards its first position. More specifically, in this exemplified embodiment, the interface or contact point between the second end portion 66 of the elongated prop 58 and the flap 60 is located on the same side of the second horizontal axle 68 as is the portion of the flap 60 covering the air inlets 70 (in FIG. 2, the contact point between the elongated prop 58 and the flap is located left of the second horizontal axle 68). Thus, the centre of mass and the force on the flap 60 provided by the elongated prop 58 will be located left (in FIG. 2) of the pivot point provided by the second horizontal axle 68, thereby keeping the flap 60 in the illustrated lowered position. As long as the flap 60 remains still, the prop 58 is also prevented from moving, thereby keeping the actuator 32 latched in its energized position. The force exerted on the flap 60 is suitably adjusted to correspond to an airflow threshold which is exceedable by a user's inhalation. A position-keeping element 72 is provided at the first end portion 62 of the prop 58. From above, the position-keeping element 72 will be in contact with the disk-shaped insert 38 (FIG. 1). That contact will ensure that the prop 58 does not accidentally pivot around the first horizontal axle 64 in case the user should turn the inhaler in a different orientation (e.g. upside down) when closing the outlet cover 12. Thus, the flap 60 and prop 58 will be able to latch the actuator 32 even if a user holds the inhaler upside down when closing the outlet cover 12.

In at least one other embodiment, the illustrated position-keeping element 72 could rather function as a biasing spring element 72. In such an embodiment, the biasing spring element 72, would not just be in contact with the disk-shaped insert 38 (FIG. 1), but would actually be pressed downwardly by the disk-shaped insert 38. This force exerted on the biasing spring element 72 would have a levering effect about the first axle 64, urging the second end portion 66 of the prop 58 in a direction towards the jaws 34 and the mouthpiece (clockwise rotation in FIG. 2). This urging of the second end portion 66, which is in contact with a mating portion of the flap 60, would keep the flap 60 biased in the illustrated substantially horizontal lowered position. The biasing force transmitted from the biasing spring element 72 to the flap 60 would suitably be adjusted to correspond to an airflow threshold which is exceedable by a user's inhalation.

In another embodiment (not shown in the Figures), the element 72 could be replaced by a spring located on the insert 38. This could be a steel spring, for example, bearing on a small projection at the top of the prop 58 in order to bias it in essentially the same way as the element 72.

Figure 3:
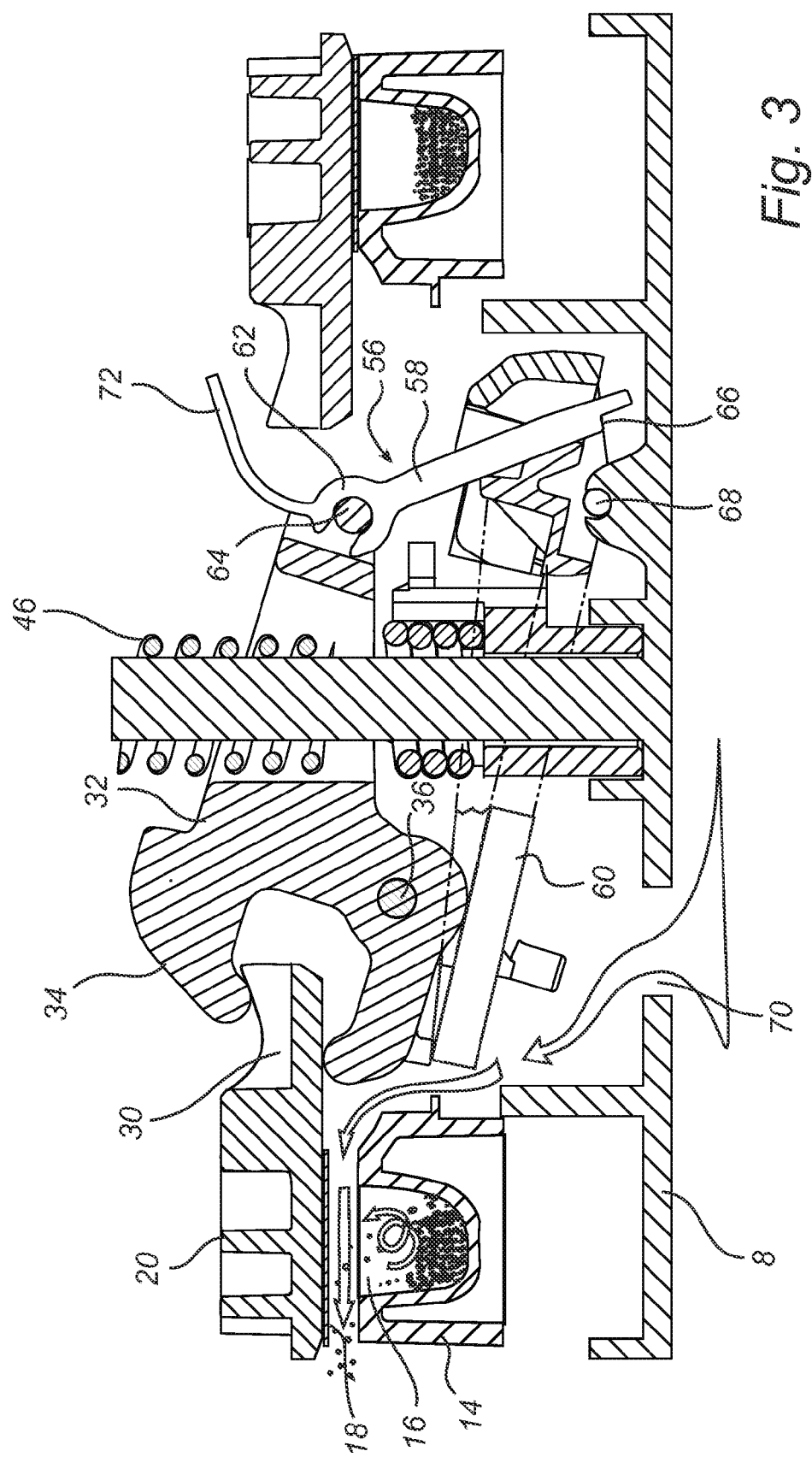
FIG. 3 illustrates, at the time of dispensing medicament from the inhaler, a cross-sectional view of selected details of the inhaler.

Thus, in order to administer a dose, the user inhales creating a sufficient airflow to raise the flap 60 against the biasing force. This is illustrated in FIG. 3. As the flap 60 is raised by the airflow and pivoted around the second axle 68 (clockwise in FIG. 3), the mating portion of the flap 60, being on the other side of the axle is lowered, whereby the second end portion 66 of the prop 58 loses its support. This will cause the prop 58 to pivot around the first axle 64 (anticlockwise in FIG. 3) and to "roll" off the mating portion of the flap 60. The latch 56 is now in its second position, in which it allows the actuator 32 to move to said unloaded position. Thus, the stored energy of the coil spring 46 will cause the now released actuator 32 to move. The actuator 32 will pivot around its axle 36 and the jaws 34 will be raised, whereby the engaged separating element 20 is lifted from the base 14. The foil portion 18 remains attached to the separating element 20, thus opening the medicament-containing cavity 16. FIG. 1 illustrates with dashed lines a separating element 20 being raised by the jaws 34 of the actuator 32.

It is realized that the design of the exemplified inhaler 2 provides for use of a phenomenon denoted as shear driven cavity principle during deaggregation of the powder in the cavity 16 and emptying of the powder therefrom. The shear driven cavity is a model for flow in a cavity where the upper boundary moves in a desired flow direction, and thus causes a rotation in the cavity. FIG. 2 illustrates a medicament powder-containing cavity 16 having a suitable headspace above the powder. In FIG. 3, the inhalation airflow passes by said headspace along a flats surface region, said flat surface region comprising the opening into the powder-containing cavity 16. The horizontal passing of the inhalation airflow leads to a build-up of an eddy air stream in the cavity 16 which causes powder to be deaggregated and emptied from the cavity 16. The cavity 16 is generally brick-shaped and the cavity opening has a rim where the sides of the cavity transcend into the flow passage flat surface region. Accordingly, the airflow, when passing the cavity in the flow passage, preferably flows in parallel with a plane coinciding with the rim of the cavity opening in the flow passage.

While the flap 60 may return to the lowered position after a dose is dispensed, the jaws 34 of the actuator 32 will remain in the unloaded position (see e.g. FIG. 7) until the user primes the inhaler for the next dose.

Although the priming of the inhaler 2 may be coupled to either the opening or closing of the outlet cover 12, in this example embodiment, it is assumed that closing of the outlet cover 12 primes the inhaler 2. Thus, when the user has inhaled a dose (FIGS. 3 and 7), he/she will close the outlet cover 12 to cover the mouthpiece 10 (FIG. 1). Although, the outlet cover 12 may be designed to form various travel paths, such as linear or stepwise paths, in this example embodiment the outlet cover 12 is rotated to cover the mouthpiece 10. During such closing of the outlet cover 12, the connected insert 38 with its force transmitting projecting member 50 and cam 44 will cause the jaws 34 of the actuator 32 to be lowered against the force of the coil spring 46 (FIG. 5) and the base 14 to be rotated, thus presenting an unopened next cavity 16 to the jaws 34. The insert 38 will also press the position-keeping element 72 of the prop 58, causing the latch 56 to return to its first position, whereby the actuator 32 is prevented from lifting its jaws 34. After that, when the user opens the outlet cover 12 in order to take another dose, the insert 38 will rotate the other way without affecting the latched and energized actuator 32. The inhaler 2 is now primed (triggered) and ready to be fired when the user breaths in through the mouthpiece 10, thereby enabling breath-triggered lifting of a foil portion 18 from a cavity 16.

In order to reduce the risk of latching the actuator 32 in the energized position without having aligned an unopened cavity 16, the latch 56 is prevented from returning to the first latching position before the next cavity is aligned with the mouthpiece 10. Also in order to reduce the risk of overindexing, i.e. passing an unopened cavity 16 past the mouthpiece 10 without opening the cavity 16, an indexing mechanism for sequentially aligning the cavities with the mouthpiece 10 is provided, wherein the indexing mechanism is adapted to align the next cavity 16 with the mouthpiece 10 after the actuator 32 has been moved from the unloaded position to the energized position.

Thus, in the illustrated example embodiment, after a dose has been dispensed, the user closes the outlet cover 12. As has been described above, the rotation of the outlet cover 12 causes the generally disk-shaped insert 38 to rotate. Through the rotation of the insert 38, the provided cam 44 will urge the actuator 32 (see FIG. 5) to move to its energized position. Thus, the jaws 34 of the actuator 32 will move from the raised unloaded position illustrated in FIGS. 3 and 7 to the lowered energized position illustrated in FIGS. 2 and 6.

Substantially simultaneously with the cam 44 urging the actuator 32, through the rotation of the insert 38, the projecting second force transmitting member 50 will urge the indexing mechanism to advance the next cavity 16 to be aligned with the mouthpiece 10. More particularly, as illustrated in FIG. 6, the projecting member 50 will energize the torsion spring 52 which is connected to the drive member 54 (see FIG. 8). The energized torsion spring 52 will urge the connected drive member 54 to rotate around the central axis provided by the post 48 (see FIG. 1) in order to engage the base 14 and to thereby cause the base 14 to rotate so as to bring the next cavity 16 aligned with the mouthpiece.

However, the force on the drive member 54 provided by the projecting member 50 via the torsion spring 52 is temporarily counteracted, at least until the actuator 32 has reached its energized position. If the jaws 34 of the actuator 32 would not be lowered before indexing, the separating element 20 next in turn would risk hitting the jaws 34 during the indexing.

Figure 5:
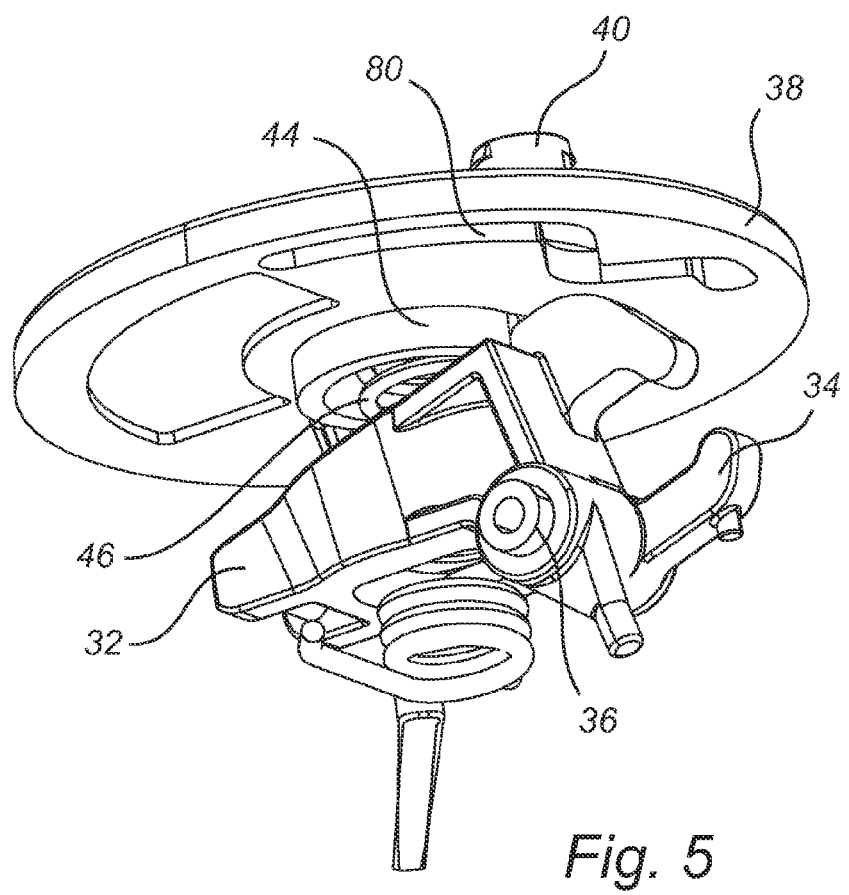
Figure 10:
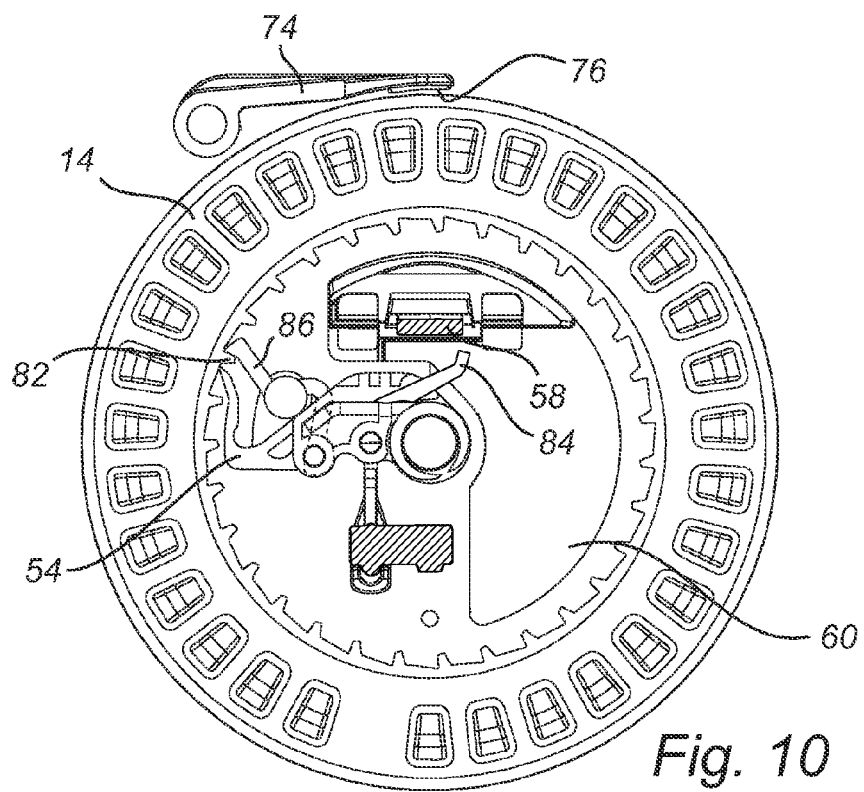
FIG. 10 is a cross-sectional view of selected details of the inhaler after indexing.
Figure 11:
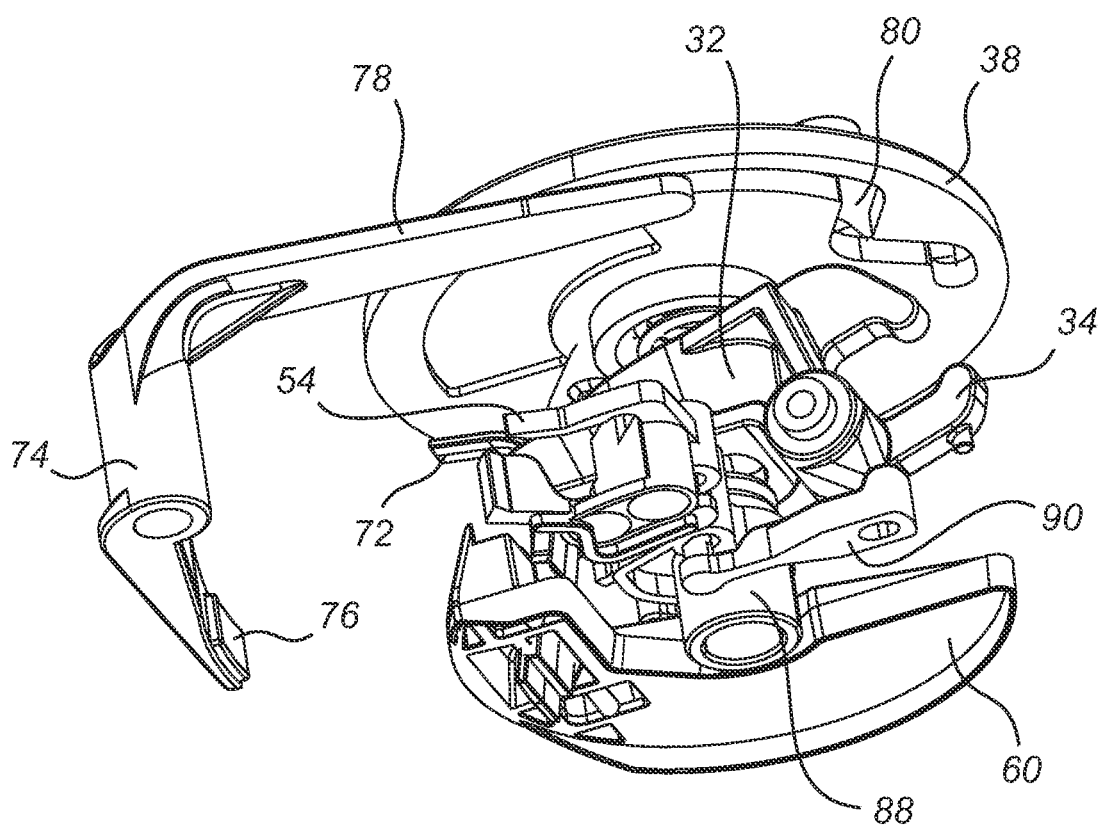

The counteracting member comprises a brake 74 adapted to prevent the compartments from moving. The brake 74 is attached to a lateral post 75 projecting from the lower housing portion 8 (see FIG. 1). The brake comprises a brake pad 76 which is pressed against the outer enveloping surface of the base 14 (see FIG. 9), thereby preventing the base 14 from rotating. The counteracting member also comprises a follower 78 (see FIGS. 1 and 11) which is connected to the brake 74 and which travels in a track 80 provided in the underside of the generally disk-shaped insert 38. The track 80 is best seen in FIGS. 4, 5 and 11, wherein FIG. 11 demonstrates how the follower 78 travels in the track 80. Thus, as the follower 78 travels in the track 80, it will follow an irregular path and when it reaches a point of release, the connected brake 74 lets go of the base 14 (FIG. 10). Now, the base 14 is allowed to be rotated by the drive member 54 which is urged by the torsion spring 52 as previously explained. Thus, the above exemplified mechanical sequencing assembly provides for alternate energizing of the opening mechanism (herein exemplified as the jawed actuator 32) and indexing of the compartments (herein exemplified as sealed cavities 16 in a base 14).

Figure 9:
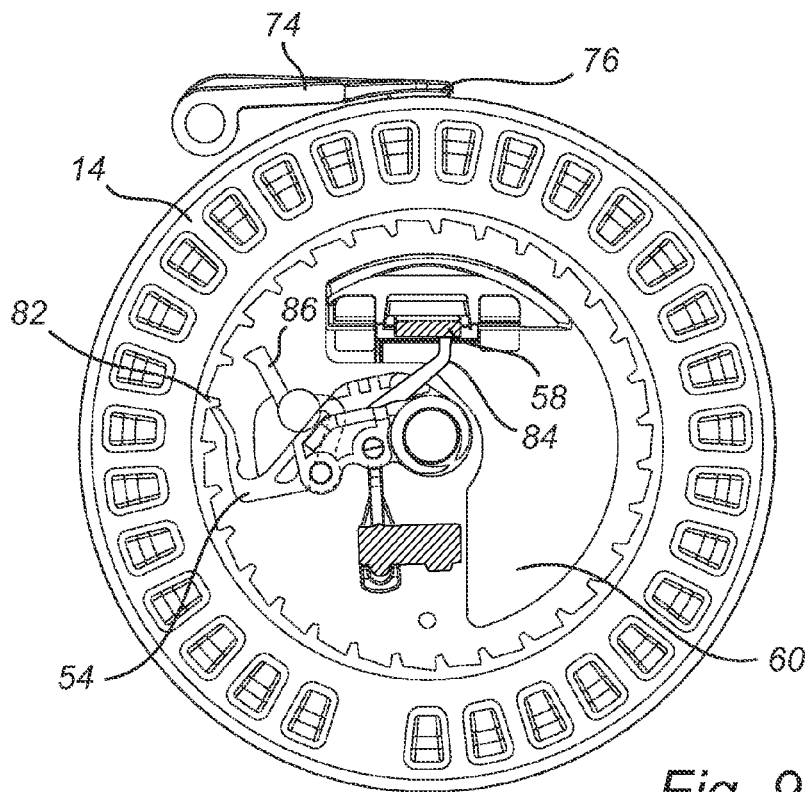
FIG. 9 is a cross-sectional view of selected details of the inhaler before indexing.

As illustrated in FIG. 9, before the brake 74 is released an end portion of the drive member 54 engages one of a plurality of teeth 82 in the base 14. An arm-shaped catch 84 is connected to the drive member 54 and may even be formed in one piece with the drive member 54. The catch 84 is in a preventing position, in which it prevents the first element (prop 58) of the latch 56 from becoming supported by the second element (flap 60) of the latch 56. Thus, in this state of the inhaler, the actuator cannot become latched in the energized position. Thus, the risk of re-firing from the same cavity 16 is reduced.

As the brake 74 is released, the drive member 54 will via the engaged tooth 82 rotate the base 14 one cavity-step. FIGS. 9 and 10 also illustrate a pawl 86 being pivotally mounted at a pivot point of the drive member (indicated with dashed lines). In FIG. 9, the pawl 86 is retracted, while in FIG. 10 the pawl 86 has been advanced to engage with a tooth 82, herein illustrated as engaged with the opposite side of the same tooth 82 that is pushed by the drive member 54. The pawl 86 prevents the drive member 54 from over-rotating the base 14, ensuring that the inhaler is indexed only one cavity-step at a time.

The drive member 54 and the catch 84 are connected to a common barrel 88 (best seen in FIG. 11) which swivels around the central post 48 (FIG. 1) projecting upwardly from the lower housing portion 8. As the drive member 54 rotates the base 14 the catch 84 will be removed from the preventing position, as illustrated in FIG. 10, thereby allowing the prop 58 to become supported by the flap 60 and latch the energized actuator. The inhaler is now primed.

As previously described, in particular in connection with FIGS. 2 and 3, when the user opens the outlet cover 12 and inhales through the mouthpiece 10, the flap 60 is raised so that the prop 58 comes off the flap 60, thereby unlatching the actuator 32. The actuator 32 being energized by the coil spring 46 will be raised so that the jaws 34 of the actuator 32 remove the separating element 20 and the foil portion 18 from the cavity 16 presently aligned with the mouthpiece 10. As can be seen in FIG. 11, a movable pulling arm 90 connects the drive member 54 with the actuator 32. As the actuator 32 and the jaws 34 are raised, the pulling arm 90 follows that motion whereby at the other end of the pulling arm 90, the drive member 54 will be pulled from the primed state shown in FIG. 10 to the fired state shown in FIG. 9. The catch 84 will consequently be moved back to its preventing position shown in FIG. 9. Next, when the user closes the outlet cover 12, the inhaler will once again become primed.

If the user, for some reason, does not close the outlet cover 12 enough, the follower 78 travelling in the track 80 will not reach its point of release, and consequently the brake 74 will not be released. This in turn means that there will be no indexing. Furthermore, although the actuator 32 is in its energized position, it will not become latched, as latching can only occur in connection with indexing, as explained above. Thus, if the user then opens the outlet cover 12, which has not been fully closed, the actuator 32 will simply move back to its unloaded position.

The herein discussed indexing mechanism, enables rotation of the base 14 to be limited to one direction. Thus, un-indexing may be prevented from occurring. This may be advantageous in connection with other types of opening mechanisms or separating elements.

It should be noted that in this application terms such as "upper", "lower", "above", "below" have been used for explanatory purposes to describe the internal relationship between elements of the inhaler, regardless of how the inhaler is oriented in the surrounding environment. For instance, in the exemplified embodiment in the drawings, the cavities 16 are regarded as being placed "below" the foil portions 18, while the separating elements 20 are regarded as being placed "above" the foil portions 18, regardless of how the inhaler 2 as a whole is held or turned by the user. Similarly, "horizontal" means a direction located in the plane of the foil portions 18 or any plane parallel to the plane of the foil portions 18, and "vertical" means any direction perpendicular to such planes. Thus, a vertical line may intersect the cavities 16, the foil portion 18 and the separating elements 20.

Most components of the inhaler 2, such as the base 14, the separating elements 20, the actuator 32 and the latch 56 are suitably made of a plastic material, such as a polymer, however, other materials, such as metal or ceramic are conceivable alternatives.

The inhaler 2 may suitably comprise a structure that provides a moisture protection, such as e.g. a moisture absorbent sink as described in WO2006/000758, or any other appropriate alternative for including desiccant material.

In a further embodiment (not shown in the figures), the cover 12 could be replaced by a cover which extends over the majority of the housing. The cover would be rotatable with respect to the housing between an open configuration in which the mouthpiece is exposed and a closed confirguration in which the mouthpiece as well as the majority of the housing is enclosed in the cover. The cover could have, formed on its internal surface, the cam surfaces 44, 50, 80 which are in previous embodiments associated with the insert 38. An aperture in the housing would be provided through which some or all of the cam surfaces, e.g. the cam surface 50, could project in order to engage with the corresponding parts of the mechanism inside the housing (e.g. indexing spring 52).

The invention claimed is:

1. An inhaler, comprising:
an outlet;
a plurality of sealed compartments containing medicament;
an opening mechanism having an energized position in which the opening mechanism is biased towards an unloaded position, wherein during movement from the energized position to the unloaded position the opening mechanism is configured to open a sealed compartment aligned with the outlet;
an indexing mechanism for sequentially aligning the compartments with the outlet, wherein the indexing mechanism is adapted to align the next compartment with the outlet after the opening mechanism has been moved from the unloaded position to the energized position;
a latch having a first position, in which the latch is configured to latch the opening mechanism in the energized position, and a second position, in which the latch is configured to allow the opening mechanism to be in said unloaded position, wherein the latch is at least partly arranged in a flow path such that an inhalation flow through the flow path affects the latch to move from the first position to the second position, wherein the latch is prevented from returning to the first position before the indexing mechanism has aligned the next compartment with the outlet; and
a catch having a preventing position, in which the catch is configured to prevent the latch from reaching the first position, and a removed position, in which the catch is configured to allow the latch to reach the first position, wherein the catch is connected to and movable with the indexing mechanism.

2. The inhaler as claimed in claim 1, further comprising:
an outlet cover movable for alternatingly closing and opening the outlet; and
a mechanical sequencing assembly connected to and movable with the outlet cover,
wherein, upon one of said closing or opening movements of the outlet cover, the mechanical sequencing assembly is configured to sequentially cause the opening mechanism to reach the energized position and then the indexing mechanism to align the next compartment with the outlet.

3. The inhaler as claimed in claim 2, wherein the mechanical sequencing assembly includes:
a first force transmitting member adapted to move the opening mechanism from the unloaded position to the energized position;
a second force transmitting member adapted to urge the indexing mechanism to advance the next compartment to be aligned with the outlet; and
a counteracting member for temporarily counteracting the effect of the second force-transmitting member until the opening mechanism has reached the energized position.

4. The inhaler as claimed in claim 3, wherein the opening mechanism further includes a first spring, wherein said first force transmitting member is configured to push the opening mechanism against the force of the first spring to provide the opening mechanism in the energized position.

5. The inhaler as claimed in claim 4, wherein the indexing mechanism includes:
a drive member configured to advance the compartments; and
a second spring connected to the drive member, wherein the second force transmitting member is adapted to energize the second spring while the counteracting member temporarily prevents the compartments from moving.

6. The inhaler as claimed in claim 5, wherein the mechanical sequencing assembly further includes a track, and the counteracting member includes a brake adapted to prevent the compartments from moving, and a follower which is connected to the brake and which travels in said track as the mechanical sequencing assembly moves in response to the movement of the outlet cover, wherein, when the follower reaches a point of release, the connected brake is released, thereby enabling the compartments to move as a result of the force provided by the energized second spring via the drive member.

7. The inhaler as claimed in claim 5, wherein the catch is connected to the drive member, wherein, when the counteracting member prevents the compartments from moving, the catch is maintained in the preventing position, and when the drive member moves the compartments, the catch is moved to the removed position.

8. The inhaler as claimed in claim 1, wherein the latch Includes a first element and a second element, the first element being connected to the opening mechanism, the second element including:
a supporting position, wherein the supporting position is configured to immobilize the first element, thereby preventing the opening mechanism from moving to the unloaded position; and
a non-supporting position, wherein the first element is configured to move, thereby allowing the biased opening mechanism to move to the unloaded position, wherein the second element is movable to the non-supporting position in response to the inhalation flow, and
wherein, in the preventing position, the catch is configured to prevent the first element from becoming supported by the second element.

9. The inhaler as claimed in claim 1, further comprising:
a base having said plurality of sealed compartments containing medicament, said compartments being in the form of cavities in the base;
a plurality of foil portions including two sides, one side being attached to the base for sealing the medicament within the respective cavities; and
a plurality of separating elements, each separating element being attached to the other side of a respective foil portion for separating the foil portion from the cavity,
wherein the opening mechanism includes an actuator configured to engage with the separating element to cause the separating element to be moved away from the cavity.

10. The inhaler as claimed in claim 1, wherein the medicament includes an active ingredient selected from one or more of mometasone, ipratropium bromide, tiotropium and salts thereof, salemeterol, fiuticasone propionate, beclomethasone dipropionate, reproterol, clenbuterol, rofleponide and salts, nedocromil, sodium cromoglycate, flunisolide, budesonide, formoterol fumarate dihydrate, terbutaline, terbutaline sulphate, salbutamol base and sulphate, fenoterol, 3-[2-(4-Hydroxy-2-oxo-3H-1,3-benzothiazol-7-yl)ethylamino]-N-[2-[2-(4-methylphenyl)ethoxy]ethyl]propanesulphonamide, hydrochloride, indacaterol, aclidinium bromide, N-[2-(Diethylamino)ethyl]-N-(2-{[2-(4-hydroxy-2- oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide); N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate); a [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate); a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate).

11. A method of priming an inhaler which comprises an outlet, a sequence of sealed compartments containing medicament, an indexing mechanism, and an opening mechanism for opening the sealed compartment which is aligned with the outlet, the method comprising:

moving the opening mechanism to an energized position in which the opening mechanism is biased towards an unloaded position;

advancing the indexing mechanism to align the next compartment with the outlet after said moving of the opening mechanism;

latching the opening mechanism in the energized position after said aligning of the next compartment; and preventing the latching of the opening mechanism with a catch before aligning of the next compartment, wherein the catch is connected to and movable with the indexing mechanism.

12. A method of dispensing a medicament from an inhaler as claimed in claim 11, further comprising:

providing an airflow through the inhaler to activate the unlatching of the opening mechanism;

unlatching the opening mechanism in response to said airflow, thereby allowing the opening mechanism to move to its unloaded position;

opening, during the movement of the opening mechanism to the unloaded position, the sealed compartment aligned with the outlet; and dispensing the medicament entrained by the airflow.

13. An inhaler, comprising:

an outlet;

a plurality of sealed compartments containing medicament;

an opening mechanism having an energized position in which the opening mechanism is biased towards an unloaded position, wherein during movement from the energized position to the unloaded position the opening mechanism is configured to open a sealed compartment aligned with the outlet;

an indexing mechanism for sequentially aligning the compartments with the outlet, wherein the indexing mechanism is adapted to align the next compartment with the outlet after the opening mechanism has been moved from the unloaded position to the energized position;

a latch having a first position, in which the latch is configured to latch the opening mechanism in the energized position, and a second position, in which the latch is configured to allow the opening mechanism to be in said unloaded position, wherein the latch is at least partly arranged in a flow path such that an inhalation flow through the flow path affects the latch to move from the first position to the second position, wherein the latch is prevented from returning to the first position before the indexing mechanism has aligned the next compartment with the outlet;

an outlet cover movable for alternatingly closing and opening the outlet; and a mechanical sequencing assembly connected to and movable with the outlet cover, wherein, upon one of said closing or opening movements of the outlet cover, the mechanical sequencing assembly is configured to sequentially cause the opening mechanism to reach the energized position and then the indexing mechanism to align the next compartment with the outlet.

\* \* \* \* \*

UNITED STATES PATENT AND TRADEMARK OFFICE
CERTIFICATE OF CORRECTION

| | | |
|---|---|---|
| PATENT NO. | : 9,155,851 B2 | Page 1 of 1 |
| APPLICATION NO. | : 13/123714 | |
| DATED | : October 13, 2015 | |
| INVENTOR(S) | : John Briant et al. | |

It is certified that error appears in the above-identified patent and that said Letters Patent is hereby corrected as shown below:

In The Claims

Claim 8, Column 20, line 27, "Includes" should read --includes--.

Claim 10, Column 20, line 59, "fiuticasone" should read --fluticasone--.

Signed and Sealed this
Eighth Day of March, 2016

Michelle K. Lee
*Director of the United States Patent and Trademark Office*